United States Patent
Mathonneau et al.

(10) Patent No.: US 10,675,236 B2
(45) Date of Patent: *Jun. 9, 2020

(54) COMPOSITION COMPRISING AT LEAST ONE ANIONIC SURFACTANT, AT LEAST ONE NONIONIC SURFACTANT, AT LEAST ONE AMPHOTERIC SURFACTANT, AT LEAST ONE CATIONIC POLYMER AND AT LEAST ONE AMPHOTERIC POLYMER

(71) Applicant: L'Oreal, Paris (FR)

(72) Inventors: Estelle Mathonneau, Saint Ouen (FR); Marie-Florence D'Arras, Saint Ouen (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/756,255

(22) PCT Filed: Sep. 1, 2016

(86) PCT No.: PCT/EP2016/070641
§ 371 (c)(1),
(2) Date: Feb. 28, 2018

(87) PCT Pub. No.: WO2017/037188
PCT Pub. Date: Mar. 9, 2017

(65) Prior Publication Data
US 2018/0250218 A1 Sep. 6, 2018

(30) Foreign Application Priority Data

Sep. 1, 2015 (FR) ..................... 15 58102
Sep. 1, 2015 (FR) ..................... 15 58104

(51) Int. Cl.
| | |
|---|---|
| *A61K 8/81* | (2006.01) |
| *A61K 8/39* | (2006.01) |
| *A61K 8/44* | (2006.01) |
| *A61K 8/46* | (2006.01) |
| *A61Q 5/02* | (2006.01) |
| *A61K 8/60* | (2006.01) |
| *A61Q 5/12* | (2006.01) |
| *A61K 8/86* | (2006.01) |

(52) U.S. Cl.
CPC .............. *A61K 8/817* (2013.01); *A61K 8/39* (2013.01); *A61K 8/442* (2013.01); *A61K 8/463* (2013.01); *A61K 8/466* (2013.01); *A61K 8/604* (2013.01); *A61K 8/8158* (2013.01); *A61K 8/86* (2013.01); *A61Q 5/02* (2013.01); *A61Q 5/12* (2013.01); *A61K 2800/5426* (2013.01); *A61K 2800/5428* (2013.01); *A61K 2800/594* (2013.01); *A61K 2800/596* (2013.01)

(58) Field of Classification Search
None
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 3,206,462 A | 9/1965 | McCarty |
| 3,874,870 A | 4/1975 | Green et al. |
| 3,910,862 A | 10/1975 | Barabas et al. |
| 3,912,808 A | 10/1975 | Sokol |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,027,021 A | 5/1977 | Underwood |
| 4,075,136 A | 2/1978 | Schaper |
| 4,157,388 A | 6/1979 | Christiansen |
| 4,165,367 A | 8/1979 | Chakrabarti |
| 4,197,865 A | 4/1980 | Jacquet et al. |
| 4,217,914 A | 8/1980 | Jacquet et al. |
| 4,349,532 A | 9/1982 | Vanlerberghe et al. |
| 4,591,610 A | 5/1986 | Grollier |
| 4,702,906 A | 10/1987 | Jacquet et al. |
| 4,719,282 A | 1/1988 | Nadolsky et al. |
| 4,761,273 A | 8/1988 | Grollier et al. |
| 2001/0009909 A1 | 7/2001 | Maubru et al. |
| 2005/0158269 A1 | 7/2005 | Simonet |
| 2007/0122369 A1* | 5/2007 | Suenaga ............... A61K 8/892 424/70.12 |
| 2011/0232668 A1 | 9/2011 | Hoffmann et al. |
| 2015/0093348 A1 | 4/2015 | Sato et al. |
| 2018/0243194 A1* | 8/2018 | Mathonneau ........... A61Q 5/02 |

FOREIGN PATENT DOCUMENTS

| | | |
|---|---|---|
| EP | 0122324 A1 | 10/1984 |
| EP | 0 416 447 A1 | 3/1991 |

(Continued)

OTHER PUBLICATIONS

International Search Report for counterpart Application No. PCT/EP2016/070641, dated Oct. 20, 2016.

(Continued)

*Primary Examiner* — Aradhana Sasan
(74) *Attorney, Agent, or Firm* — The Marbury Law Group, PLLC

(57) ABSTRACT

The present invention relates to a composition for cleansing and conditioning keratin fibres, in particular human keratin fibers such as the hair, comprising one or more anionic surfactants, one or more nonionic surfactants in a content of at least 3% by weight relative to the total weight of the composition, one or more amphoteric surfactants in a content of at least 3% by weight relative to the total weight of the composition, one or more particular cationic polymers and one or more amphoteric polymers. The invention also relates to a process for cleansing and conditioning keratin fibres and also to a use involving said composition.

14 Claims, No Drawings

(56) References Cited

FOREIGN PATENT DOCUMENTS

| | | | |
|---|---|---|---|
| EP | 1132079 | A1 | 9/2001 |
| EP | 1557155 | A1 | 7/2005 |
| FR | 2077143 | A5 | 10/1971 |
| FR | 2080759 | A1 | 11/1971 |
| FR | 2190406 | A2 | 2/1974 |
| FR | 2270846 | A1 | 12/1975 |
| FR | 2316271 | A1 | 1/1977 |
| FR | 2320330 | A1 | 3/1977 |
| FR | 2336434 | A1 | 7/1977 |
| FR | 2393573 | A1 | 1/1979 |
| FR | 2413907 | A1 | 8/1979 |
| FR | 2505348 | A1 | 11/1982 |
| FR | 2542997 | A1 | 9/1984 |
| GB | 1546809 | A | 5/1979 |
| JP | S58-138799 | A | 8/1983 |
| JP | H10-36232 | A | 2/1998 |
| JP | 2004-035524 | A | 2/2004 |
| JP | 2005-232169 | A | 9/2005 |
| JP | 2006-151871 | A | 6/2006 |
| JP | 2007-176895 | A | 7/2007 |
| JP | 2008-297295 | A | 12/2008 |
| WO | 00/37041 | A1 | 6/2000 |
| WO | 2017/037187 | A1 | 3/2017 |

OTHER PUBLICATIONS

Porter, M.R., "Handbook of Surfactants," published by Blackie & Son (Glasgow and London), 1991, pp. 116-178.
International Search Report for counterpart Application No. PCT/EP2016/070640, dated Oct. 21, 2016.
Written Opinion for counterpart Application No. PCT/EP2016/070640, dated Oct. 21, 2016.
Mintel, "Shampoo," XP002756429, May 2006.
Anonymous, "Conditioning Polymers Provide Multiple Benefits," XP002662657, Internet Citation: Mar. 1, 2011, pp. 1-3, retrieved from Internet: http://www.personalcaremagazine.com/Pring.aspx?Story=7939 (retrieved on Oct. 21, 2011).
Japanese Office Action for counterpart Application No. 2018-511380, dated Mar. 4, 2019—English Translation.
Japanese Office Action for counterpart Application No. 2018-529744, dated Mar. 4, 2019, English Translation.

\* cited by examiner

COMPOSITION COMPRISING AT LEAST ONE ANIONIC SURFACTANT, AT LEAST ONE NONIONIC SURFACTANT, AT LEAST ONE AMPHOTERIC SURFACTANT, AT LEAST ONE CATIONIC POLYMER AND AT LEAST ONE AMPHOTERIC POLYMER

CROSS REFERENCE TO RELATED APPLICATIONS

This is a national stage application of PCT/EP2016/070641, filed internationally on Sep. 1, 2016, which claims priority to French Application Nos. 1558102, filed on Sep. 1, 2015, and U.S. Pat. No. 1,558,104, filed on Sep. 1, 2015, all of which are incorporated by reference herein in their entireties.

The present invention relates to a composition for cleansing and conditioning keratin fibres, in particular human keratin fibres such as the hair, comprising one or more anionic surfactants, one or more nonionic surfactants in a total content of at least 3% by weight relative to the total weight of the composition, one or more amphoteric surfactants in a total content of at least 3% by weight relative to the total weight of the composition, one or more particular cationic polymers and one or more amphoteric polymers.

The invention also relates to a process for cleansing and conditioning keratin fibres and also to a use involving said composition.

It is common practice to use detergent compositions (such as shampoos) based essentially on standard surfactants especially of anionic, nonionic and/or amphoteric type, but more particularly of anionic type, for cleansing and/or washing keratin fibres such as the hair. These compositions are applied to wet hair and the foam generated by massaging or rubbing with the hands makes it possible, after rinsing with water, to remove the diverse types of soiling initially present on the hair or the skin.

These detergent compositions do, admittedly, have good washing power, but the cosmetic properties thereby imparted still remain to be improved, especially when they are applied to sensitized hair, i.e. hair that is generally damaged or embrittled by the action of external atmospheric agents, such as light and bad weather, and/or mechanical or chemical treatments, such as brushing, combing, dyeing, bleaching, permanent waving and/or relaxing.

Moreover, these compositions have a relatively aggressive nature since their application may result in the long run in more or less pronounced damage on the hair fibre associated in particular with the gradual removal of the lipids or proteins contained in or at the surface of said fibre.

Thus, it is often common practice to resort to care compositions using complementary cosmetic agents known as conditioning agents in order to improve the cosmetic properties of sensitized hair. These conditioning agents may, of course, also improve the cosmetic behaviour of natural hair.

These care compositions are especially hair conditioners, which may be in the form of hair gels or lotions or more or less thick creams.

However, the cationic surfactants used in such care compositions, especially in hair conditioners, are difficult to use in detergent compositions on account of their incompatibility with anionic surfactants.

In particular, their incompatibility with anionic surfactants may give rise to stabilization difficulties for the detergent compositions and have an impact on their working qualities, especially in terms of foaming power and/or start of foaming.

Furthermore, the presence of cationic surfactants in the detergent compositions may lead, after one or more applications to the hair, to heaviness or overcharging of the head of hair (which is known as the build-up effect), thus having a negative impact on the cosmetic properties imparted.

Moreover, such care compositions give the hair cosmetic properties that may fade out after the application of one or more non-treating shampoos.

There is thus a real need to develop compositions for cleansing and conditioning keratin fibres, which do not have all of the drawbacks mentioned above, i.e. which are capable of imparting improved cosmetic properties, after one or more applications, without making the head of hair charged or heavy, while at the same time maintaining good washing power and satisfactory working qualities.

This aim is achieved by the present invention, one subject of which is especially a cosmetic composition, preferably a hair composition, intended especially for cleansing and conditioning keratin fibres, in particular human keratin fibres such as the hair, comprising one or more anionic surfactants, one or more nonionic surfactants in a total content of at least 3% by weight relative to the total weight of the composition, one or more amphoteric surfactants in a total content of at least 3% by weight relative to the total weight of the composition, one or more cationic polymers with a cationic charge density of greater than or equal to 4 meq./g and one or more polymers chosen from amphoteric polymers and/or cationic polymers with a cationic charge density of less than 4 meq./g.

Specifically, the composition according to the invention makes it possible to improve the cosmetic properties imparted to the keratin fibres, especially to the hair, preferably sensitized hair. In particular, the composition according to the invention makes it possible to improve the disentangling, the suppleness and also the feel of the hair, without a build-up effect.

Furthermore, the composition according to the invention may impart cosmetic properties that are shampoo-resistant.

The composition according to the invention also has the advantage of being stable on storage both at room temperature (20-25° C.) and at 45° C., especially as regards its visual aspect and/or its viscosity.

For the purposes of the present invention, the term "stable" refers to a composition which, after two months of storage at 25 to 45° C., shows no change in appearance, colour, odour or viscosity.

The composition may be transparent; it may also be pearlescent, where appropriate.

The composition according to the invention may also have satisfactory foaming power.

The composition according to the invention also makes it possible to apply conditioning agents, such as cationic or amphoteric polymers, in an amount sufficient to obtain adequate cosmetic conditioning properties.

Preferably, the composition according to the invention is non-colouring.

According to the present invention, the term "non-colouring composition" means a composition not containing any dye for keratin fibres, such as direct dyes or oxidation dye precursors (bases and/or couplers). If they are present, their content does not exceed 0.005% by weight, relative to the total weight of the composition. Specifically, at such a content, only the composition would be dyed, i.e. no dyeing effect would be observed on the keratin fibres.

The invention thus relates to a composition comprising the compounds as defined above.

The composition according to the invention especially comprises one or more polymers chosen from amphoteric polymers, cationic polymers with a cationic charge density of less than 4 meq./g, and a mixture thereof.

The present invention also relates to a process for washing and conditioning keratin fibres, in particular human keratin fibres such as the hair, comprising the application to said fibres of a composition according to the invention.

The invention also relates to the use of the composition according to the invention as a shampoo for washing and conditioning the hair.

Other subjects, characteristics, aspects and advantages of the invention will emerge even more clearly on reading the description and the examples that follow.

In the text hereinbelow, and unless otherwise indicated, the limits of a range of values are included in that range, in particular in the expressions "between" and "ranging from . . . to . . . ".

Moreover, the expression "at least one" used in the present description is equivalent to the expression "one or more".

Anionic Surfactants

As indicated above, the composition comprises one or more anionic surfactants.

For the purposes of the present invention, the term "anionic surfactant" means a surfactant comprising, as ionic or ionizable groups, only anionic groups. These anionic groups are preferably chosen from the groups $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$, $POH$ and $PO^-$.

Preferably, the anionic surfactants used in the composition according to the invention are chosen from anionic surfactants comprising in their structure one or more sulfate and/or sulfonate and/or phosphate and/or carboxylate groups, and/or mixtures thereof.

Preferentially, the composition according to the invention comprises one or more carboxylic alkyl ether anionic surfactants.

More preferentially, the composition according to the invention comprises a mixture of anionic surfactants and especially one or more anionic surfactants comprising in their structure one or more sulfate and/or sulfonate and/or phosphate groups and one or more carboxylic alkyl ether anionic surfactants.

The anionic surfactant(s) comprising in their structure one or more sulfate and/or sulfonate and/or phosphate groups may be oxyethylenated and/or oxypropylenated. The total average number of ethylene oxide (EO) and/or propylene oxide (PO) groups may then range from 1 to 50 and especially from 1 to 10.

The anionic surfactant(s) comprising in their structure one or more sulfate and/or sulfonate and/or phosphate groups may be chosen from alkyl sulfates, alkylamido sulfates, alkyl ether sulfates, alkylamido ether sulfates, alkylaryl ether sulfates, alkyl ether sulfosuccinates, acyl isethionates and methyl acyl taurates, olefin sulfonates, and salts thereof; the alkyl or acyl group of all these various compounds preferably containing from 8 to 24 carbon atoms, and the aryl group preferably denoting a phenyl or benzyl group.

Among the anionic surfactants comprising in their structure one or more sulfate and/or sulfonate and/or phosphate groups, it is preferred to use one or more anionic sulfate surfactants, preferentially chosen from $C_8$-$C_{14}$ and more particularly $C_{12}$-$C_{14}$ alkyl ether sulfates, and/or one or more olefin sulfonates.

Preferably, the anionic surfactant(s) comprising in their structure one or more sulfate and/or sulfonate and/or phosphate groups are in the form of salts, and in particular of alkaline salts, especially sodium salts, ammonium salts, amine salts, including amino alcohol salts, and/or magnesium salts. These salts preferably comprise from 2 to 5 ethylene oxide groups.

Among these salts, sodium, triethanolamine, magnesium or ammonium ($C_{12}$-$C_{14}$)alkyl sulfates and/or sodium, ammonium or magnesium ($C_{12}$-$C_{14}$)alkyl ether sulfates, which are oxyethylenated, for example with 1 or 2.2 mol of ethylene oxide, or sodium olefin sulfonates, are more preferably used.

Better still, the surfactant(s) comprising in their structure one or more sulfate and/or sulfonate and/or phosphate groups are chosen from sodium, ammonium or magnesium ($C_{12}$-$C_{14}$)alkyl ether sulfates oxyethylenated with 2.2 mol of ethylene oxide, as sold under the name Texapon N702 by the company Cognis.

Among the anionic surfactant(s) comprising in their structure one or more sulfate and/or sulfonate and/or phosphate groups, it is preferred to use sodium or ammonium lauryl ether sulfates or sodium olefin sulfonates.

The carboxylic alkyl ether anionic surfactant(s) that may be used according to the invention preferably comprise a $C_6$-$C_{24}$ alkyl chain.

The carboxylic alkyl ether anionic surfactant(s) may be chosen, alone or as mixtures, from:
($C_6$-$C_{24}$)alkyl ether carboxylic acids,
($C_6$-$C_{24}$)alkylaryl ether carboxylic acids,
($C_6$-$C_{24}$)alkylamido ether carboxylic acids,
and salts thereof.

The carboxylic alkyl ether anionic surfactant(s) may be oxyalkylenated, preferably oxyethylenated and/or oxypropylenated. The total average number of alkylene oxide groups then preferably ranges from 2 to 50, in particular from 2 to 24 and better still from 2 to 15.

When the carboxylic alkyl ether anionic surfactant(s) are oxyalkylenated, they preferably comprise from 2 to 50 alkylene oxide groups and in particular from 2 to 50 ethylene oxide (EO) groups.

Preferably, the carboxylic alkyl ether anionic surfactant(s) are neutralized with one or more salts. The salts are chosen in particular from alkaline salts and especially sodium salts, ammonium salts, amine salts, including amino alcohol salts such as triethanolamine or monoethanolamine salts, and magnesium salts.

The polyethoxylated carboxylic anionic surfactants more preferably used are those corresponding to formula (I) below:

$$R_1(OC_2H_4)_nOCH_2COOA \qquad (I)$$

in which:
$R_1$ represents a linear or branched $C_8$-$C_{22}$ alkyl or alkenyl group or mixture of groups, a ($C_8$-$C_9$)alkylphenyl group, a group $R_2CONH$—$CH_2$—$CH_2$— with $R_2$ denoting a linear or branched $C_{11}$-$C_{21}$ alkyl or alkenyl group,
n is an integer or decimal number (average value) that may range from 2 to 24 and preferably from 2 to 15,
A denotes H, $NH_4$, Na, K, Li, Mg or a monoethanolamine or triethanolamine residue. Mixtures of compounds of formula (I) may also be used, in particular mixtures in which the groups $R_1$ are different.

Preferably, $R_1$ denotes a group or a mixture of groups chosen from $C_{12}$-$C_{14}$ alkyl, cocoyl, oleyl, nonylphenyl and octylphenyl groups; A denotes a hydrogen or sodium atom; and n ranges from 2 to 20 and preferably from 2 to 10.

Even more preferentially, use is made of compounds of formula (I) in which $R_1$ denotes a $C_{12}$ alkyl group, A denotes a hydrogen or sodium atom and n ranges from 2 to 10.

Among the commercial products that may preferably be used are the products sold by the company KAO under the names:

Akypo® NP 70 ($R_1$=nonylphenyl, n=7, A=H)
Akypo® NP 40 ($R_1$=nonylphenyl, n=4, A=H)
Akypo® OP 40 ($R_1$=octylphenyl, n=4, A=H)
Akypo® OP 80 ($R_1$=octylphenyl, n=8, A=H)
Akypo® OP 190 ($R_1$=octylphenyl, n=19, A=H)
Akypo® RLM 38 ($R_1$=($C_{12}$-$C_{14}$)alkyl, n=4, A=H)
Akypo® RLM 38 NV ($R_1$=($C_{12}$-$C_{14}$)alkyl, n=4, A=Na)
Akypo® RLM 45 CA ($R_1$=($C_{12}$-$C_{14}$)alkyl, n=4.5, A=H)
Akypo® RLM 45 NV ($R_1$=($C_{12}$-$C_{14}$)alkyl, n=4.5, A=Na)
Akypo® RLM 100 ($R_1$=($C_{12}$-$C_{14}$)alkyl, n=10, A=H)
Akypo® RLM 100 NV ($R_1$=($C_{12}$-$C_{14}$)alkyl, n=10, A=Na)
Akypo® RLM 130 ($R_1$=($C_{12}$-$C_{14}$)alkyl, n=13, A=H)
Akypo® RLM 160 NV ($R_1$=($C_{12}$-$C_{14}$)alkyl, n=16, A=Na)
or by the company Sandoz under the names:
Sandopan DTC-Acid ($R_1$=($C_{13}$)alkyl, n=6, A=H)
Sandopan DTC ($R_1$=($C_{13}$)alkyl, n=6, A=Na)
Sandopan LS 24 ($R_1$=($C_{12}$-$C_{14}$)alkyl, n=12, A=Na)
Sandopan JA 36 ($R_1$=($C_{13}$)alkyl, n=18, A=H),
and more particularly the products sold under the following names:
Akypo® RLM 45 (INCI: Laureth-5 carboxylic acid)
Akypo® RLM 100
Akypo® RLM 38.

Among the carboxylic alkyl ether anionic surfactants, use is preferably made of lauryl ether carboxylic acids or sodium lauryl ether carboxylates.

Preferably, the anionic surfactants are chosen from sulfate anionic surfactants, chosen especially from $C_8$-$C_{14}$ alkyl ether sulfates and carboxylic alkyl ether surfactants.

Preferentially, the composition according to the invention comprises one or more carboxylic alkyl ether surfactants corresponding to formula (I).

More preferably, the composition according to the invention comprises a mixture of sulfate anionic surfactants, chosen especially from $C_8$-$C_{14}$ and more particularly $C_{12}$-$C_{14}$ alkyl ether sulfates, and carboxylic alkyl ether surfactants corresponding to formula (I) as described previously.

The anionic surfactant(s) may be present in the composition according to the invention in a total content ranging from 1% to 20% by weight, preferably in a content ranging from 2% to 18% by weight and better still from 4% to 15% by weight relative to the total weight of the composition.

Nonionic Surfactants

As indicated above, the composition comprises one or more nonionic surfactants in a total content of greater than or equal to at least 3% by weight relative to the total weight of the composition.

The nonionic surfactant(s) present in the composition according to the invention are described, for example, in the Handbook of Surfactants by M. R. Porter, published by Blackie & Son (Glasgow and London), 1991, pp. 116-178.

Examples of nonionic surfactants that may be mentioned include the following nonionic surfactants:

oxyalkylenated ($C_8$-$C_{24}$)alkylphenols;
saturated or unsaturated, linear or branched, oxyalkylenated or glycerolated $C_8$-$C_{40}$ alcohols, preferably comprising one or two fatty chains;
saturated or unsaturated, linear or branched, oxyalkylenated $C_8$-$C_{30}$ fatty acid amides;
esters of saturated or unsaturated, linear or branched, $C_8$-$C_{30}$ acids and of polyethylene glycols;
preferably oxyethylenated esters of saturated or unsaturated, linear or branched, $C_8$-$C_{30}$ acids and of sorbitol;
esters of fatty acids and of sucrose;
($C_8$-$C_{30}$)alkyl(poly)glucosides, ($C_8$-$C_{30}$)alkenyl(poly)glucosides, which are optionally oxyalkylenated (0 to 10 oxyalkylene units) and comprising from 1 to 15 glucose units, ($C_8$-$C_{30}$)alkyl (poly)glucoside esters;
saturated or unsaturated oxyethylenated vegetable oils;
condensates of ethylene oxide and/or of propylene oxide;
N—($C_8$-$C_{30}$)alkylglucamine and N—($C_8$-$C_{30}$)acylmethylglucamine derivatives;
aldobionamides;
amine oxides;
oxyethylenated and/or oxypropylenated silicones;
and mixtures thereof.

The oxyalkylene units are more particularly oxyethylene or oxypropylene units, or their combination, preferably oxyethylene units.

The number of moles of ethylene oxide and/or of propylene oxide preferably ranges from 1 to 250, more particularly from 2 to 100 and better still from 2 to 50; the number of moles of glycerol ranges in particular from 1 to 50 and better still from 1 to 10.

Advantageously, the nonionic surfactants according to the invention do not comprise any oxypropylene units.

By way of example of glycerolated nonionic surfactants, use is preferably made of monoglycerolated or polyglycerolated $C_8$-$C_{40}$ alcohols comprising from 1 to 50 mol of glycerol, preferably from 1 to 10 mol of glycerol.

Mention may be made, as examples of compounds of this type, of lauryl alcohol comprising 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol and octadecanol comprising 6 mol of glycerol.

Among the glycerolated alcohols, it is more particularly preferred to use the $C_8$ to $C_{10}$ alcohol containing 1 mol of glycerol, the $C_{10}$ to $C_{12}$ alcohol containing 1 mol of glycerol and the $C_{12}$ alcohol containing 1.5 mol of glycerol.

The nonionic surfactant(s) used in the composition according to the invention are preferentially chosen from:

saturated or unsaturated, linear or branched, oxyethylenated $C_8$-$C_{40}$ alcohols comprising from 1 to 100 mol of ethylene oxide, preferably from 2 to 50 and more particularly from 2 to 40 mol of ethylene oxide and preferably comprising one or two fatty chains;
saturated or unsaturated oxyethylenated vegetable oils comprising from 1 to 100 and preferably from 2 to 50 mol of ethylene oxide;
($C_8$-$C_{30}$)alkyl(poly)glucosides, which are optionally oxyalkylenated (0 to 10 OE) and comprising 1 to 15 glucose units;
monoglycerolated or polyglycerolated $C_8$ to $C_{40}$ alcohols, comprising from 1 to 50 mol of glycerol and preferably from 1 to 10 mol of glycerol;
saturated or unsaturated, linear or branched, oxyalkylenated $C_8$-$C_{30}$ fatty acid amides;
esters of saturated or unsaturated, linear or branched, $C_8$-$C_{30}$ acids and of polyethylene glycols;

preferably oxyethylenated esters of saturated or unsaturated, linear or branched, $C_8$-$C_{30}$ acids and of sorbitol; and mixtures thereof.

More preferentially, the nonionic surfactants are chosen from saturated or unsaturated, linear or branched, oxyethylenated $C_8$ to $C_{40}$ alcohols comprising from 1 to 100 mol of ethylene oxide, preferably from 2 to 50, more particularly from 2 to 40 mol, or even from 3 to 20 mol of ethylene oxide and comprising at least one $C_8$-$C_{20}$ and especially $C_{10}$-$C_{18}$ alkyl chain; especially lauryl alcohol containing 4 mol of ethylene oxide (INCI name: Laureth-4) and lauryl alcohol containing 12 mol of ethylene oxide (INCI name: Laureth-12).

Thus, the nonionic surfactants are preferentially chosen from oxyethylenated $C_8$-$C_{20}$ alcohols comprising from 2 to 50 and in particular from 3 to 20 mol of ethylene oxide.

Preferably, the nonionic surfactant(s) are present in a total content ranging from 3% to 20% by weight, more preferentially in a content ranging from 4% to 15% by weight relative to the total weight of the composition, better still from 4.5% to 12% by weight.

Amphoteric Surfactants

As indicated above, the composition comprises one or more amphoteric surfactants in a total content of greater than or equal to at least 3% by weight relative to the total weight of the composition.

In particular, the amphoteric or zwitterionic surfactant(s), which are preferably non-silicone, used in the composition according to the present invention may especially be derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group.

Mention may in particular be made of $(C_8$-$C_{20})$alkyl betaines, $(C_8$-$C_{20})$alkyl sulfobetaines, $(C_8$-$C_{20})$alkylamido $(C_3$-$C_8)$alkyl betaines and $(C_8$-$C_{20})$alkylamido$(C_6$-$C_8)$alkyl sulfobetaines.

Among the optionally quaternized derivatives of secondary or tertiary aliphatic amines that can be used, as defined above, mention may also be made of the compounds with respective structures (II) and (III) below:

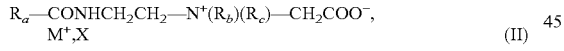

$$R_a\text{—CONHCH}_2\text{CH}_2\text{—N}^+(R_b)(R_c)\text{—CH}_2\text{COO}^-,\ M^+,X\qquad (II)$$

in which formula:
  $R_a$ represents a $C_{10}$ to $C_{30}$ alkyl or alkenyl group derived from an acid $R_a$COOH preferably present in hydrolysed coconut oil, or a heptyl, nonyl or undecyl group;
  $R_b$ represents a beta-hydroxyethyl group; and
  $R_c$ represents a carboxymethyl group;
  $M^+$ represents a cationic counterion resulting from an alkali metal or alkaline-earth metal, such as sodium, an ammonium ion or an ion resulting from an organic amine; and
  $X^-$ represents an organic or mineral anionic counterion, such as that chosen from halides, acetates, phosphates, nitrates, $(C_1$-$C_4)$alkyl sulfates, $(C_1$-$C_4)$alkyl- or $(C_1$-$C_4)$alkylarylsulfonates, in particular methyl sulfate and ethyl sulfate; or alternatively $M^+$ and $X^-$ are absent;

$$R_{a'}\text{—CONHCH}_2\text{CH}_2\text{—N(B)(B')}\qquad (III)$$

in which formula:
  B represents the group —$CH_2CH_2OX'$;
  B' represents the group —$(CH_2)_zY'$, with z=1 or 2;

X' represents the group —$CH_2COOH$, —$CH_2$—COOZ', —$CH_2CH_2COOH$, —$CH_2CH_2$—COOZ', or a hydrogen atom;
  Y' represents the group —COOH, —COOZ' or —$CH_2CH(OH)SO_3H$ or the group $CH_2CH(OH)SO_3$—Z';
  Z' represents a cationic counterion resulting from an alkali metal or alkaline-earth metal, such as sodium, an ammonium ion or an ion resulting from an organic amine;
  $R_{a'}$ represents a $C_{10}$ to $C_{30}$ alkyl or alkenyl group of an acid $R_{a'}$—COOH which is preferably present in coconut oil or in hydrolysed linseed oil, or an alkyl group, especially a $C_{17}$ group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of the compounds of formula (IV):

$$R_{a''}\text{—NHCH}(Y'')\text{—}(CH_2)_n\text{CONH}(CH_2)_{n'}\text{—N}(R_d)(R_e)\qquad (IV)$$

in which formula (IV):
  Y" represents the group —COOH, —COOZ" or —$CH_2$—$CH(OH)SO_3H$ or the group $CH_2CH(OH)$ $SO_3$—Z";
  $R_d$ and $R_e$ represent, independently of each other, a $C_1$ to $C_4$ alkyl or hydroxyalkyl radical;
  Z" represents a cationic counterion resulting from an alkali metal or alkaline-earth metal, such as sodium, an ammonium ion or an ion resulting from an organic amine;
  $R_{a''}$ represents a $C_{10}$-$C_{30}$ alkyl or alkenyl group of an acid $R_{a''}$—COOH which is preferably present in coconut oil or in hydrolysed linseed oil;
  n and n' denote, independently of each other, an integer ranging from 1 to 3.

Mention may be made, among the compounds of formula (II), of the compound classified in the CTFA dictionary under the name sodium diethylaminopropyl cocoaspartamide and sold by Chimex under the name Chimexane HB.

These compounds can be used alone or as mixtures.

Among the amphoteric or zwitterionic surfactants mentioned above, use is preferably made of $(C_8$-$C_{20})$alkylbetaines such as cocoylbetaine, $(C_8$-$C_{20})$alkylamido$(C_3$-$C_8)$ alkylbetaines such as cocamidopropylbetaine, and mixtures thereof, and the compounds of formula (IV) such as the sodium salt of diethylaminopropyl laurylaminosuccinamate (INCI name: sodium diethylaminopropyl cocoaspartamide).

Preferentially, the amphoteric or zwitterionic surfactants are chosen from $(C_8$-$C_{20})$alkylamido$(C_3$-$C_8)$alkylbetaines such as cocamidopropyl betaine.

Preferably, the amphoteric surfactant(s) are present in a total content ranging from 3% to 20% by weight, more preferentially in a content ranging from 3.3% to 15% by weight and better still from 3.5% to 10% by weight relative to the total weight of the composition.

Cationic Polymers

The cosmetic composition also comprises one or more cationic polymers with a cationic charge density of greater than or equal to 4 milliequivalents/gram (meq./g) and, optionally, one or more cationic polymers with a cationic charge density of less than 4 milliequivalents/gram.

The cationic charge density of a polymer corresponds to the number of moles of cationic charges per unit mass of polymer under conditions in which it is totally ionized. It may be determined by calculation if the structure of the polymer is known, i.e. the structure of the monomers constituting the polymer and their molar proportion or weight proportion. It may also be determined experimentally by the Kjeldahl method.

For the purposes of the present invention, the term "cationic polymer" denotes any polymer containing cationic groups and/or groups that can be ionized into cationic groups.

The cationic polymers with a charge density of greater than or equal to 4 meq./g that are preferred, and, when they are present, the cationic polymers with a cationic charge density of less than 4 meq./g are chosen from those that contain units comprising primary, secondary, tertiary and/or quaternary amine groups that can either form part of the main polymer chain or be borne by a side substituent directly attached thereto.

The cationic polymers used generally have a number-average molecular mass of between 500 and $5 \times 10^6$ approximately and preferably between $10^3$ and $3 \times 10^6$ approximately.

Among the cationic polymers, mention may more particularly be made of polymers of the polyamine, polyaminoamide and polyquaternary ammonium type.

These are known products. They are especially described in French patents 2 505 348 and 2 542 997. Among said polymers, mention may be made of:

The cationic polymers with a cationic charge density of greater than or equal to 4 meq./g and the cationic polymers with a cationic charge density of less than 4 milliequivalents/gram may be chosen from the following families:

(1) Homopolymers or copolymers derived from acrylic or methacrylic esters or amides and comprising at least one of the units of formula (IX), (X), (XI) or (XII) below:

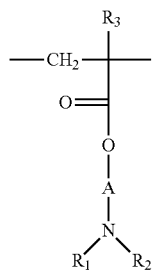

(IX)

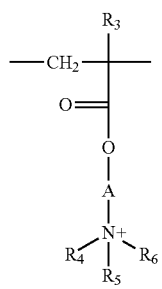

(X)

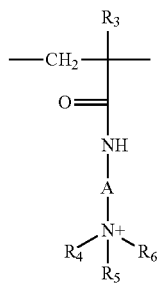

(XI)

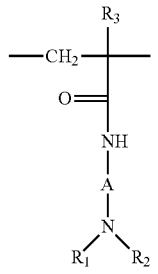

(XII)

in which:
$R_3$, which may be identical or different, denote a hydrogen atom or a $CH_3$ radical;
A, which may be identical or different, represent a linear or branched alkyl group of 1 to 6 carbon atoms, preferably 2 or 3 carbon atoms, or a hydroxyalkyl group of 1 to 4 carbon atoms;
$R_4$, $R_5$ and $R_6$, which may be identical or different, represent an alkyl group containing from 1 to 18 carbon atoms or a benzyl radical and preferably an alkyl group containing from 1 to 6 carbon atoms;
$R_1$ and $R_2$, which may be identical or different, represent hydrogen or an alkyl group containing from 1 to 6 carbon atoms, and preferably methyl or ethyl;
X denotes an anion derived from a mineral or organic acid, such as a methosulfate anion or a halide such as chloride or bromide.

Mention may be made in particular of the ethyltrimethylammonium methacrylate chloride homopolymer.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these polymers of family (1), mention may be made of:
copolymers of acrylamide and of dimethylaminoethyl methacrylate quaternized with dimethyl sulfate or with a dimethyl halide,
copolymers of acrylamide and of methacryloyloxyethyltrimethylammonium chloride,
the copolymer of acrylamide and of methacryloyloxyethyltrimethylammonium methosulfate,
quaternized or non-quaternized vinylpyrrolidone/dialkylaminoalkyl acrylate or methacrylate copolymers.

These polymers are described in detail in French patents 2 077 143 and 2 393 573,
dimethylaminoethyl methacrylate/vinylcaprolactam/vinylpyrrolidone terpolymers, vinylpyrrolidone/methacrylamidopropyldimethylamine copolymers, quaternized vinylpyrrolidone/dimethylaminopropylmethacrylamide copolymers, the crosslinked polymers of methacryloyloxy($C_1$-$C_4$) alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, in particular methylenebisacrylamide. Use may more particularly be made of a crosslinked acrylamide/methacryloyloxyethyltrimethylammonium chloride copolymer (20/80 by weight) in the form of a dispersion containing 50% by weight of said copolymer in mineral oil. This dispersion is sold under the name Salcare® SC 92 by the company Ciba. Use may also be made of a crosslinked homopolymer of methacryloyloxyethyltrimethylammonium chloride comprising approximately 50% by weight of the homopolymer in mineral oil or in a liquid ester. These dispersions are sold under the names Salcare® SC 95 and Salcare® SC 96 by the company Ciba.

(2) Cyclopolymers of alkyldiallylamine or of dialkyldiallylammonium, such as homopolymers or copolymers comprising, as main constituent of the chain, units corresponding to formula (XIII) or (XIV):

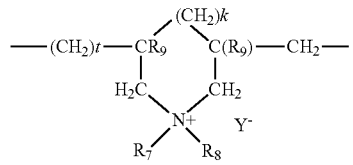

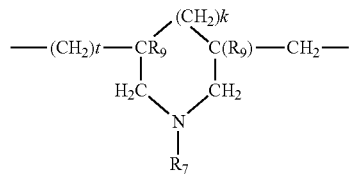

in which formulae k and t are equal to 0 or 1, the sum k+t being equal to 1; $R_9$ denotes a hydrogen atom or a methyl radical; $R_7$ and $R_8$, independently of each other, denote an alkyl group containing from 1 to 6 carbon atoms, a hydroxyalkyl group in which the alkyl group preferably contains 1 to 5 carbon atoms, or a lower ($C_1$-$C_4$) amidoalkyl group, or $R_7$ and $R_8$ may denote, together with the nitrogen atom to which they are attached, heterocyclic groups, such as piperidyl or morpholinyl; $R_7$ and $R_8$, independently of each other, preferably denote an alkyl group containing from 1 to 4 carbon atoms; $Y^-$ is an anion such as bromide, chloride, acetate, borate, citrate, tartrate, bisulfate, bisulfite, sulfate or phosphate. These polymers are in particular described in French patent 2 080 759 and in its Certificate of Addition 2 190 406.

Among the polymers defined above, mention may be made more particularly of the dimethyldiallylammonium chloride homopolymer sold under the name Merquat 100 by the company Nalco (and its homologues of low weight-average molecular mass).

(3) The quaternary diammonium polymer containing repeating units corresponding to formula (XV):

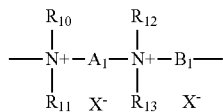

in which formula (XV):

$R_{10}$, $R_{11}$, $R_{12}$ and $R_{13}$, which may be identical or different, represent aliphatic, alicyclic or arylaliphatic radicals containing from 1 to 6 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

A1 and B1 represent polymethylene groups containing from 2 to 8 carbon atoms, which may be linear or branched and saturated or unsaturated and may contain, bonded to or intercalated in the main chain, one or more aromatic rings, or one or more oxygen or sulfur atoms, or sulfoxide, sulfone, disulfide, amino, alkylamino, hydroxyl, quaternary ammonium, ureido, amide or ester groups, and $X^-$ denotes an anion derived from a mineral or organic acid;

A1, $R_{10}$ and $R_{12}$ can form, with the two nitrogen atoms to which they are attached, a piperazine ring; in addition, if A1 denotes a linear or branched, saturated or unsaturated alkylene or hydroxyalkylene radical, B1 can also denote a group —($CH_2$)n-CO-D-OC—($CH_2$)n- in which D denotes:

a) a glycol residue of formula: —O—Z—O—, where Z denotes a linear or branched hydrocarbon-based radical or a group corresponding to one of the following formulae:

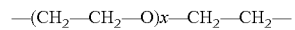

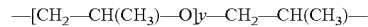

where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon-based radical, or else the divalent radical

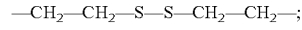

d) a ureylene group of formula: —NH—CO—NH—.

Preferably, $X^-$ is an anion, such as chloride or bromide.

These polymers have a number-average molecular mass generally between 1000 and 100 000.

Polymers of this type are especially described in French patents 2 320 330, 2 270 846, 2 316 271, 2 336 434 and 2

413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that are formed from repeating units corresponding to formula (XVI) below:

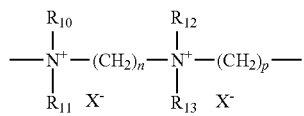

(XVI)

in which R10, R11, R12 and R13, which may be identical or different, denote an alkyl or hydroxyalkyl radical containing from 1 to 4 carbon atoms approximately, n and p are integers ranging from 2 to 8 approximately, and $X_-$ is an anion derived from a mineral or organic acid. Mention may be made in particular of Mexomer PO sold by the company Chimex.

(4) Polyquaternary ammonium polymers formed from repeating units of formula (XVII):

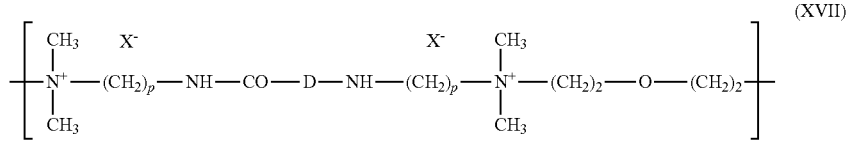

(XVII)

in which p denotes an integer ranging from 1 to 6 approximately, D may be nothing or may represent a group —(CH$_2$)$_r$—CO— in which r denotes a number equal to 4 or 7, and $X_-$ is an anion.

Such polymers may be prepared according to the processes described in U.S. Pat. Nos. 4,157,388, 4,702,906 and 4,719,282. They are especially described in patent application EP-A-122 324.

Among these polymers, examples that may be mentioned include the products Mirapol A 15, Mirapol AD1, Mirapol AZ1 and Mirapol 175 sold by the company Miranol.

(5) Quaternary polymers of vinylpyrrolidone and of vinylimidazole.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

The cationic polymers according to the invention are thus preferentially chosen from polymers with a cationic charge density of greater than or equal to 4 meq./g belonging to families (1) to (5) mentioned above.

Among all the cationic polymers that may be used in the context of the present invention, it is preferred to use polymers of the family of cyclopolymers of alkyldiallylamine or of dialkyldiallylammonium (2).

Preferably, the cationic polymer(s) are chosen from cyclopolymers of alkyldiallylamine or of dialkyldiallylammonium, such as homopolymers or copolymers comprising, as main constituent of the chain, units corresponding to formula (XIII) or (XIV).

Preferentially, the cationic polymers with a cationic charge density of greater than or equal to 4 meq./g are chosen from dialkyldiallylammonium halide homopolymers, more particularly the dialkyldiallylammonium chloride homopolymer (INCI name: Polyquaternium-6) sold under the name Merquat® 100 by the company Nalco.

Preferentially, the cationic polymers with a cationic charge density of less than 4 meq./g are chosen from copolymers of dimethyldiallylammonium chloride and of acrylamide (INCI name: Polyquaternium-7) sold under the name Merquat® 550 or Merquat 7SPR (INCI name: Polyquaternium-7) by the company Nalco.

The content of cationic polymer(s) with a charge density of greater than or equal to 4 meq./g may range from 0.05% to 5% by weight relative to the total weight of the composition, preferably from 0.1% to 3% by weight and more preferentially from 0.2% to 1.5% by weight relative to the total weight of the composition.

According to an embodiment, the total content of cationic polymer(s) in the composition according to the invention may range from 0.05% to 5% by weight relative to the total weight of the composition, preferably from 0.1% to 3% by weight and more preferentially from 0.2% to 2% by weight relative to the total weight of the composition.

In particular, when the composition comprises one or more cationic polymers with a cationic charge density of greater than or equal to 4 meq./g and one or more cationic polymers with a cationic charge density of less than or equal to 4 meq./g, then:
  the cationic polymers according to the invention with a cationic charge density of greater than or equal to 4 meq./g may be present in a content ranging from 0.01% to 5% by weight, preferably in a content ranging from 0.05% to 3% by weight and better still from 0.1% to 1.5% by weight relative to the total weight of the composition, and
  the cationic polymers according to the invention with a cationic charge density of less than 4 meq./g are present in a content ranging from 0.01% to 5% by weight, preferably in a content ranging from 0.05% to 3% by weight and better still from 0.1% to 1.5% by weight relative to the total weight of the composition.

Amphoteric Polymer

The cosmetic composition may also comprise one or more amphoteric polymers.

The amphoteric (or zwitterionic) polymers that may be used in accordance with the invention may be chosen from polymers comprising units B and C distributed randomly in the polymer chain, in which B denotes a unit derived from a monomer comprising at least one basic nitrogen atom and C denotes a unit derived from an acid monomer comprising one or more carboxylic or sulfonic groups, or alternatively B and C may denote groups derived from carboxybetaine or sulfobetaine zwitterionic monomers; B and C may also denote a cationic polymer chain comprising primary, secondary, tertiary or quaternary amine groups, in which at least one of the amine groups bears a carboxylic or sulfonic group connected via a hydrocarbon-based radical or alternatively B and C form part of a chain of a polymer containing an ethylene-a,b-dicarboxylic unit in which one of the carboxylic groups has been made to react with a polyamine comprising one or more primary or secondary amine groups.

Preferably, the amphoteric polymers that may be used according to the invention comprise the repetition:
(i) of one or more units from an acrylamide-type monomer,
(ii) of one or more units from an acrylamidoalkyltrialkylammonium-type monomer,
(iii) of one or more units derived from a monomer of (meth)acrylic acid type.

Preferably, the units derived from a monomer of acrylamide type in the amphoteric polymer are units having the structure (XVIII) below:

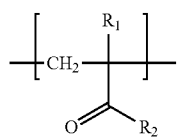

(XVIII)

in which:
$R_1$ denotes H or $CH_3$,
$R_2$ is chosen from an amino, dimethylamino, tert-butylamino or dodecylamino radical, or —NH—$CH_2OH$.

Preferably, the amphoteric polymer of the invention comprises the repetition of only one unit of formula (XVIII).

The unit derived from a monomer of acrylamide type of formula (XVIII) in which $R_1$ denotes H and $R_2$ is an amino radical is particularly preferred. It corresponds to the acrylamide monomer itself.

Preferably also, the units derived from a monomer of acrylamidoalkyltrialkylammonium type in the amphoteric polymer are units having the structure (XIX) below:

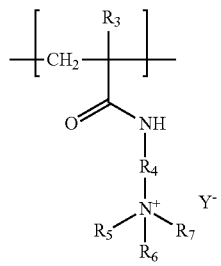

(XIX)

in which:
$R_3$ denotes H or $CH_3$,
$R_4$ denotes a $(CH_2)_k$ group with k an integer ranging from 1 to 6 and preferably from 2 to 4;
$R_5$ and $R_6$ and $R_7$, which may be identical or different, each denote an alkyl group containing from 1 to 4 carbon atoms;
$Y^-$ is an anion such as bromide, chloride, acetate, borate, citrate, tartrate, bisulfate, bisulfite, sulfate or phosphate.

Among these units derived from a monomer of acrylamidoalkyltrialkylammonium type, the ones that are preferred are those derived from the methacrylamidopropyltrimethylammonium chloride monomer, for which $R_3$ denotes a methyl radical, k is equal to 3, $R_5$, $R_6$ and $R_7$ denote a methyl radical, and $Y^-$ denotes a chloride anion.

Preferably, the amphoteric polymer of the invention comprises the repetition of only one unit of formula (XIX).

Finally, the units derived from a monomer of (meth) acrylic acid type in the amphoteric polymer are preferentially chosen from units of formula (XX):

(XX)

in which:
$R_8$ denotes H or $CH_3$,
$R_9$ denotes a hydroxyl radical or a radical —NH—$C(CH_3)_2$—$CH_2$—$SO_3H$.

The preferred units of formula (XX) correspond to the acrylic acid, methacrylic acid and 2-acrylamino-2-methylpropanesulfonic acid monomers.

Preferably, the unit derived from a monomer of (meth) acrylic acid type is that derived from acrylic acid, for which $R_8$ denotes a hydrogen atom and $R_9$ denotes a hydroxyl radical.

Preferably, the amphoteric polymer of the invention comprises the repetition of only one unit of formula (XX).

According to a preferred embodiment of the invention, the amphoteric polymer(s) comprise at least 30 mol % of units derived from a monomer of acrylamide type.

Preferably, amphoteric polymers comprise from 30 mol % to 70 mol % of units derived from a monomer of acrylamide type, more preferably from 40 mol % to 60 mol %.

The contents of units derived from a monomer of acrylamidoalkyltrialkylammonium type may advantageously be as follows: from 10 mol % to 60 mol % and preferentially from 20 mol % to 55 mol %.

The contents of units derived from a monomer of (meth) acrylic acid type may advantageously be as follows: from 1 mol % to 20 mol % and preferentially from 5 mol % to 15 mol %.

According to a preferred embodiment of the invention, the amphoteric polymer comprises:
from 30 mol % to 70 mol % of units derived from a monomer of acrylamide type, more preferably from 40 mol % to 60 mol %,
from 10 mol % to 60 mol %, preferentially from 20 mol % to 55 mol % of units derived from a monomer of acrylamidoalkyltrialkylammonium type,
from 1 mol % to 20 mol % and preferentially from 5 mol % to 15 mol % of units derived from a monomer of (meth)acrylic acid type.

The amphoteric polymer(s) according to the present invention may also comprise additional units, other than the units derived from a monomer of acrylamide type, of acrylamidoalkyltrialkylammonium type and of (meth) acrylic acid type.

According to a preferred embodiment of the invention, the amphoteric polymer(s) are constituted solely of units derived from monomers (i) of acrylamide type, (ii) of acrylamidoalkyltrialkylammonium type and (iii) of (meth) acrylic acid type.

Mention may be made, as an example of particularly preferred amphoteric polymers, of acrylamide/methacrylamidopropyltrimethylammonium/acrylic acid terpolymers. Such polymers are listed in the CTFA International Cosmetic Ingredient Dictionary, 10th edition 2004, as Polyquaternium 53. Corresponding products are especially sold under the name Merquat 2003 by the company Lubrizol.

The amphoteric polymer according to the invention may conventionally be prepared by polymerization starting with its various monomers, according to techniques known to those skilled in the art and especially by radical polymerization.

The amphoteric polymer(s) are generally present in the composition according to the invention in an amount of between 0.05% and 5% by weight, preferably between 0.1% and 3% by weight, and more particularly between 0.2% and 1.5% by weight, relative to the total weight of the composition.

According to a preferred embodiment, the composition according to the invention comprises:
  one or more anionic surfactants,
  one or more nonionic surfactants in a total content of at least 3% by weight relative to the total weight of the composition,
  one or more amphoteric surfactants in a total content of at least 3% by weight relative to the total weight of the composition,
  one or more cationic polymers with a cationic charge density of greater than or equal to 4 meq./g, and
  one or more amphoteric polymers.

According to a particular embodiment, the composition according to the invention comprises:
  one or more carboxylic alkyl ether anionic surfactants, preferably of formula (I) as defined above,
  one or more nonionic surfactants, in a total content of at least 3% by weight relative to the total weight of the composition, comprising one or more oxyethylenated $C_8$ to $C_{40}$ alcohols comprising from 2 to 50 mol of ethylene oxide and preferably comprising at least one $C_8$-$C_{20}$ alkyl chain,
  one or more amphoteric surfactants, in a total content of at least 3% by weight relative to the total weight of the composition, comprising one or more surfactants chosen from ($C_8$-$C_{20}$)alkylbetaines, ($C_8$-$C_{20}$)alkylsulfobetaines, ($C_8$-$C_{20}$)alkylamido($C_3$-$C_8$)alkylbetaines and ($C_8$-$C_{20}$)alkylamido($C_6$-$C_8$)alkylsulfobetaines,
  one or more cationic polymers with a cationic charge density of greater than or equal to 4 meq./g, chosen from dialkyldiallylammonium halide homopolymers, and
  one or more amphoteric polymers constituted solely of units derived from monomers (i) of acrylamide type, (ii) of acrylamidoalkyltrialkylammonium type and (iii) of (meth)acrylic acid type.

According to a second particular embodiment, the composition according to the invention comprises:
  one or more anionic surfactants chosen from sulfate anionic surfactants, especially from $C_8$-$C_{14}$ alkyl ether sulfates and carboxylic alkyl ether surfactants,
  one or more nonionic surfactants, in a total content of at least 3% by weight relative to the total weight of the composition, chosen from oxyethylenated $C_8$ to $C_{40}$ alcohols comprising from 2 to 50 mol of ethylene oxide and comprising at least one $C_8$-$C_{20}$ alkyl chain,
  one or more amphoteric surfactants, in a total content of at least 3% by weight relative to the total weight of the composition, chosen from ($C_8$-$C_{20}$)alkylbetaines, ($C_8$-$C_{20}$)alkylsulfobetaines, ($C_8$-$C_{20}$)alkylamido($C_3$-$C_8$)alkylbetaines and ($C_8$-$C_{20}$)alkylamido($C_6$-$C_8$)alkylsulfobetaines, and
  one or more cationic polymers with a cationic charge density of greater than or equal to 4 meq./g, chosen from diallyldialkylammonium halide homopolymers, and
  one or more amphoteric polymers constituted solely of units derived from monomers (i) of acrylamide type, (ii) of acrylamidoalkyltrialkylammonium type and (iii) of (meth)acrylic acid type.

In accordance with this second embodiment, the composition preferentially comprises a mixture of sulfate anionic surfactants, chosen especially from $C_8$-$C_{14}$ and more particularly $C_{12}$-$C_{14}$ alkyl ether sulfates, and carboxylic alkyl ether surfactants corresponding to formula (I) as defined previously.

In accordance with these two particular embodiments, the amphoteric surfactants are preferably chosen from ($C_8$-$C_{20}$)alkylamido($C_3$-$C_8$)alkylbetaines.

In accordance with these two particular embodiments, the cationic polymers with a charge density of greater than or equal to 4 meq./g may be chosen from dialkyldiallylammonium chloride homopolymers, in particular the diallyldimethylammonium chloride homopolymer.

According to another embodiment, the composition according to the invention comprises:
  one or more anionic surfactants,
  one or more nonionic surfactants in a total content of at least 3% by weight relative to the total weight of the composition,
  one or more amphoteric surfactants in a total content of at least 3% by weight relative to the total weight of the composition,
  one or more cationic polymers with a cationic charge density of greater than or equal to 4 meq./g, and
  one or more cationic polymers with a cationic charge density of less than 4 meq./g.

According to a particular embodiment, the composition according to the invention comprises:
  one or more carboxylic alkyl ether anionic surfactants, preferably of formula (I) as defined above,
  one or more nonionic surfactants, in a total content of at least 3% by weight relative to the total weight of the composition, comprising one or more oxyethylenated $C_8$ to $C_{40}$ alcohols comprising from 2 to 50 mol of ethylene oxide and comprising at least one $C_8$-$C_{20}$ alkyl chain,
  one or more amphoteric surfactants, in a total content of at least 3% by weight relative to the total weight of the composition, comprising one or more surfactants chosen from ($C_8$-$C_{20}$)alkylbetaines, ($C_8$-$C_{20}$)alkylsulfobetaines, ($C_8$-$C_{20}$)alkylamido($C_3$-$C_8$)alkylbetaines and ($C_8$-$C_{20}$)alkylamido($C_6$-$C_8$)alkylsulfobetaines,
  one or more cationic polymers with a cationic charge density of greater than or equal to 4 meq./g, chosen from dialkyldiallylammonium halide homopolymers, and
  one or more cationic polymers with a cationic charge density of less than 4 meq./g, chosen from copolymers of diallyldimethylammonium halide and of acrylamide.

According to a second particular embodiment, the composition according to the invention comprises:
  one or more anionic surfactants chosen from sulfate anionic surfactants, especially from $C_8$-$C_{14}$ alkyl ether sulfates and carboxylic alkyl ether surfactants, one or more nonionic surfactants, in a total content of at least 3% by weight relative to the total weight of the composition, chosen from oxyethylenated $C_8$ to $C_{40}$ alcohols comprising from 2 to 50 mol of ethylene oxide and comprising at least one $C_8$-$C_{20}$ alkyl chain, one or more amphoteric surfactants, in a total content of at least 3% by weight relative to the total weight of the composition, chosen from ($C_8$-$C_{20}$)alkylbetaines, ($C_8$-$C_{20}$)alkylsulfobetaines, ($C_8$-$C_{20}$)alkylamido($C_3$-$C_8$)alkylbetaines and ($C_8$-$C_{20}$)alkylamido($C_6$-$C_8$)alkylsulfobetaines, and one or more cationic polymers with a cationic charge density of greater than or equal to 4 meq./g, chosen from diallyldialkylammonium halide homopolymers, and one or more cationic polymers with a cationic charge density of less than 4 meq./g, chosen from copolymers of diallyldialkylammonium halide and of acrylamide.

In accordance with this second particular embodiment, the composition preferentially comprises a mixture of sulfate anionic surfactants, chosen especially from $C_8$-$C_{14}$ and more particularly $C_{12}$-$C_{14}$ alkyl ether sulfates, and carboxylic alkyl ether surfactants corresponding to formula (I) as defined previously.

In accordance with these two particular embodiments, the amphoteric surfactants are preferably chosen from ($C_8$-$C_{20}$)alkylamido($C_3$-$C_8$)alkylbetaines.

In accordance with these two particular embodiments, the cationic polymers with a cationic charge density of greater than or equal to 4 meq./g may be chosen from dialkyldiallylammonium chloride homopolymers, in particular the diallyldimethylammonium chloride homopolymer, and the cationic polymers with a cationic charge density of less than 4 meq./g may be chosen from copolymers of diallyldimethylammonium chloride and of acrylamide.

According to another embodiment, the composition according to the invention comprises:
one or more anionic surfactants,
one or more nonionic surfactants in a total content of at least 3% by weight relative to the total weight of the composition,
one or more amphoteric surfactants in a total content of at least 3% by weight relative to the total weight of the composition,
one or more cationic polymers with a cationic charge density of greater than or equal to 4 meq./g, and
one or more cationic polymers with a cationic charge density of less than 4 meq./g, and
one or more amphoteric polymers.

The composition according to the invention may comprise water or a mixture of water and one or more cosmetically acceptable solvents selected from $C_1$-$C_4$ lower alcohols, such as ethanol, isopropanol, tert-butanol or n-butanol; polyols such as glycerol, propylene glycol and polyethylene glycols; and mixtures thereof.

The pH of the compositions according to the invention generally ranges from 3 to 10, preferably from 3.5 to 7 and better still from 4 to 5.5.

The composition according to the invention may also comprise one or more standard additives that are well known in the art, such as natural or synthetic thickeners or viscosity regulators; $C_{12}$-$C_{30}$ fatty alcohols; ceramides; fatty esters such as isopropyl myristate, myristyl myristate, cetyl palmitate and stearyl stearate; mineral, plant or synthetic oils such as α-olefins or avocado oil, rapeseed oil, apricot oil, camelina oil or liquid petroleum jelly; vitamins or provitamins; nonionic or anionic polymers; pH stabilizers, preserving agents; dyes; fragrances or anti-dandruff agents.

The thickener(s) may be chosen from cellulose-based thickeners, for example hydroxyethylcellulose, hydroxypropylcellulo se and carboxymethylcellulose, guar gum and derivatives thereof, for example the hydroxypropyl guar sold by the company Rhodia under the reference Jaguar HP 105, gums of microbial origin, such as xanthan gum and scleroglucan gum, synthetic thickeners such as crosslinked acrylic acid or acrylamidopropanesulfonic acid homopolymers, for example Carbomer, nonionic, anionic, cationic or amphoteric associative polymers, such as the polymers sold under the names Pemulen TR1 or TR2 by the company Goodrich, Salcare SC90 by the company Ciba, Aculyn 22, 28, 33, 44 or 46 by the company Röhm & Haas, and Elfacos T210 and T212 by the company Akzo.

A person skilled in the art will take care to select the optional additives and the amount thereof such that they do not harm the properties of the compositions of the present invention.

These additives are generally present in the composition according to the invention in an amount ranging from 0 to 20% by weight relative to the total weight of the composition.

The compositions in accordance with the invention may be used as shampoos for washing and conditioning the hair, and they are preferably applied in this case to wet hair in amounts that are effective for washing them, and the lather generated by massaging or rubbing with the hands may then be removed, after an optional leave-on time, by rinsing with water, the operation possibly being repeated one or more times.

Process and Use According to the Invention

Another subject of the present invention relates to a process for washing and conditioning keratin fibres, in particular human keratin fibres such as the hair, comprising the application to said fibres of a composition according to the invention as defined above.

Preferably, the process for washing and conditioning keratin fibres, in particular human keratin fibres such as the hair, comprises the application to said fibres of a composition comprising:
one or more anionic surfactants,
one or more nonionic surfactants in a total content of at least 3% by weight relative to the total weight of the composition,
one or more amphoteric surfactants in a total content of at least 3% by weight relative to the total weight of the composition,
one or more cationic polymers with a cationic charge density of greater than or equal to 4 meq./g, and
one or more amphoteric polymers.

Preferably, the process for washing and conditioning keratin fibres, in particular human keratin fibres such as the hair, comprises the application to said fibres of a composition comprising:
one or more anionic surfactants,
one or more nonionic surfactants in a total content of at least 3% by weight relative to the total weight of the composition,
one or more amphoteric surfactants in a total content of at least 3% by weight relative to the total weight of the composition,
one or more cationic polymers with a cationic charge density of greater than or equal to 4 meq./g, and
one or more cationic polymers with a cationic charge density of less than 4 meq./g.

Preferably, the process for washing and conditioning keratin fibres, in particular human keratin fibres such as the hair, comprises the application to said fibres of a composition comprising:
- one or more anionic surfactants,
- one or more nonionic surfactants in a total content of at least 3% by weight relative to the total weight of the composition,
- one or more amphoteric surfactants in a total content of at least 3% by weight relative to the total weight of the composition,
- one or more cationic polymers with a cationic charge density of greater than or equal to 4 meq./g, and
- one or more cationic polymers with a cationic charge density of less than 4 meq./g, and one or more amphoteric polymers.

The composition may be applied to wet or dry hair, and preferably to wet or moist hair.

The composition is preferably applied to sensitized hair.

According to one embodiment, the process consists in applying to keratin fibres an effective amount of the composition according to the invention, optionally massaging the fibres, optionally leaving the composition to stand on the fibres, and rinsing.

The leave-on time of the composition on the keratin fibres may be between a few seconds and 15 minutes and preferably between 30 seconds and 5 minutes. The composition is generally rinsed out with water.

An optional step of drying the keratin fibres may be performed.

The present invention also relates to the use of the composition according to the invention as described previously for washing and conditioning keratin fibres, in particular human keratin fibres such as the hair.

The examples that follow serve to illustrate the invention without, however, being limiting in nature.

I. EXAMPLES

The cosmetic compositions according to the invention are prepared from the ingredients indicated in the table below, the amounts of which are expressed as weight percentages relative to the total weight of the composition.

|  | A | B | C | D | E | F | G | H | Comp |
|---|---|---|---|---|---|---|---|---|---|
| Alkylpolyglucoside | — | — | — | — | — | — | 5.1 | 5.67 | 4 |
| Laureth-12 | — | 5 | 5 | 4 | 4 | 4 | — | — | — |
| Laureth-4 | 5 | 5 | 5 | 1 | 1 | 1 | — | — | 1 |
| Polysorbate 20 | 5 | — | — | — | — | — | — | — | — |
| Carboxylic acid Laureth-5 | 6.3 | 6.3 | 6.3 | 6 | 6 | 6 | 0.9 | 1 | 6 |
| Cocamidopropyl betaine | 3.8 | 3.8 | 3.8 | 7 | 7 | 7 | 6.3 | 7 | 7 |
| Sodium laureth sulfate | 1.75 | 1.75 | 1.75 | 7 | 7 | — | 9 | 10 | 7 |
| Sodium ($C_{14}$-$C_{16}$)olefin sulfonate | — | — | — | — | — | 7 | — | — | — |
| Polyquaternium-6 | 1 | 1 | 0.5 | 0.5 | 1 | 0.5 | 0.5 | 0.5 | 0.75 |
| Polyquaternium-53 | 0.5 | 0.5 | 0.25 | 0.25 | 0.5 | 0.25 | 0.25 | 0.25 | — |
| Sodium chloride | — | 1 | 1 | 0.7 | 0.7 | 0.7 | 1 | 0.5 | 0.7 |
| Salicylic acid | 0.2 | 0.2 | 0.2 | 0.2 | 0.2 | 0.2 | 0.2 | 0.2 | 0.2 |
| Sodium benzoate | 0.5 | 0.5 | 0.5 | 0.5 | 0.5 | 0.5 | 0.5 | 0.5 | 0.5 |
| Sodium hydroxide/citric acid | qs pH = 5 ± 0.5 | qs pH = 5 ± 0.5 | qs pH = 5 ± 0.5 | qs pH = 5 ± 0.5 | qs pH = 6 ± 0.5 | qs pH = 6 ± 0.5 | qs pH = 5 ± 0.5 | qs pH = 5 ± 0.5 | qs pH = 5 ± 0.5 |
| Water | qs 100 | qs 100 | qs 100 | qs 100 | qs 100 | qs 100 | qs 100 | qs 100 | qs 100 |

The compositions are applied to locks of moderately sensitized hair (SA20) at a rate of 0.37 g of composition per gram of hair. They are then worked with the fingers five times and then rinsed ten times under a tap at a flow rate of 4 l/minute with water at 38° C.

A panel of 5 experts compared the feel and the ease of the disentangling on wet hair, of locks treated with formulations A to H relative to those treated with the comparative formulation.

All the experts noted a better cosmetic quality of the feel and also better ease of the disentangling for compositions A to H compared with the comparative formula.

The compositions according to the invention are prepared from the ingredients indicated in the table below, the amounts of which are expressed as weight percentages relative to the total weight of the composition.

|  | Reference 1 | Reference 2 | A |
|---|---|---|---|
| Lauryl ether carboxylic acid (4.5 OE) | 6 | 6 | 6 |
| Cocoylamidopropylbetaine | 7 | 7 | 7 |
| Oxyethylenated lauric acid (4 OE) | 1 | 1 | 1 |
| Oxyethylenated (12 EO) lauryl alcohol | 4 | 4 | 4 |
| Sodium lauryl ether sulfate | 7 | 7 | 7 |
| Polydimethyldiallylammonium chloride Polyquaternium-6 | 0.75 | — | 0.5 |
| Acrylic acid/MAPTAC/acrylamide terpolymer Polyquaternium-53 | — | 0.75 | 0.25 |
| Sodium chloride | 0.8 | 0.8 | 0.8 |
| Sodium benzoate | 0.5 | 0.5 | 0.5 |
| Salicylic acid | 0.2 | 0.2 | 0.2 |
| Citric acid | qs pH 4.7 | qs pH 4.7 | qs pH 4.7 |
| Water | qs 100 | qs 100 | qs 100 |

The compositions are applied to locks of moderately sensitized hair (SA20) at a rate of 0.37 g of formulation/g of hair.

They are then worked with the fingers five times and then rinsed ten times under a tap at a flow rate of 4 l/minute with water at 38° C.

A panel of 5 experts compared the feel and the ease of the disentangling on wet hair, of locks treated with formulation A relative to those treated with the comparative formulations (Reference 1/Reference 2).

II. EXAMPLES—A2 VS REFERENCE 3/4 a. Preparation of the Compositions

The following compositions are prepared from the ingredients indicated in the table below, the amounts of which are expressed as weight percentages relative to the total weight of the composition.

|  | Reference 3 | Reference 4 | A2 |
|---|---|---|---|
| Oxyethylenated lauric acid (4 OE) | 5 | 5 | 5 |
| Polysorbate 20 | 5 | 5 | 5 |
| Laureth-5 carboxylic acid | 6.3 | 6.3 | 6.3 |
| Cocamidopropylbetaine | 3.8 | 3.8 | 3.8 |
| Sodium laureth sulfate | 1.75 | 1.75 | 1.75 |
| Polydimethyldiallylammonium chloride Polyquaternium-6 | 1 | — | 1 |
| Polyquaternium-53 | — | 0.5 | 0.5 |
| Sodium chloride | 0.5 | 0.5 | 0.5 |
| Salicylic acid | 0.2 | 0.2 | 0.2 |
| Sodium benzoate | 0.5 | 0.5 | 0.5 |
| Sodium hydroxide/ Citric acid | qs pH 5 ± 0.5 | qs pH 5 ± 0.5 | qs pH 5 ± 0.5 |
| Water | qs 100 | qs 100 | qs 100 |

The compositions have a clear appearance, at the time of manufacture (t=t0), at room temperature.

The compositions are applied to locks of moderately sensitized hair (SA20) at a rate of 0.37 g of formulation/g of hair.

They are then worked with the fingers five times and then rinsed ten times under a tap at a flow rate of 4 l/minute with water at 38° C.

b. Results

A panel composed of 5 testers compared the feel on wet hair, of locks treated with formulation A2 relative to those treated with the comparative compositions (Reference 3/Reference 4).

Each tester evaluated the feel by classifying each of the locks treated with the comparative compositions (Reference 3/Reference 4) and the composition according to the invention (composition A2).

|  | Reference 3 | Reference 4 | A2 |
|---|---|---|---|
| Tester 1 | 2 | 3 | 1 |
| Tester 2 | 2 | 3 | 1 |
| Tester 3 | 2 | 3 | 1 |
| Tester 4 | 2 | 3 | 1 |
| Tester 5 | 2 | 3 | 1 |
| Overall classification | 2 | 3 | 1 |

The composition according to the invention (Composition A2) was systematically classified by the panel of testers as giving a smoother feel to the locks of treated hair than the comparative compositions (Reference 3/Reference 4).

III. EXAMPLE—A3 VS REFERENCE 5/6

The following compositions are prepared from the ingredients indicated in the table below, the amounts of which are expressed as weight percentages relative to the total weight of the composition.

|  | Reference 5 | Reference 6 | A3 |
|---|---|---|---|
| Laureth-12 | 4 | 4 | 4 |
| Oxyethylenated lauric acid (4 OE) | 6 | 6 | 6 |
| Laureth-5 carboxylic acid | 6.3 | 6.3 | 6.3 |
| Cocamidopropylbetaine | 3.8 | 3.8 | 3.8 |
| Sodium laureth sulfate | 1.75 | 1.75 | 1.75 |
| Polydimethyldiallylammonium chloride Polyquaternium-6 | 1 | — | 1 |
| Polyquaternium-53 | — | 0.5 | 0.5 |
| Sodium chloride | 0.5 | 0.5 | 0.5 |
| Salicylic acid | 0.2 | 0.2 | 0.2 |
| Sodium benzoate | 0.5 | 0.5 | 0.5 |
| Sodium hydroxide/ Citric acid | qs pH 5 ± 0.5 | qs pH 5 ± 0.5 | qs pH 5 ± 0.5 |
| Water | qs 100 | qs 100 | qs 100 |

The compositions have a clear appearance, at the time of manufacture (t=t0), at room temperature.

The compositions are applied to locks of moderately sensitized hair (SA20) at a rate of 0.37 g of formulation/g of hair.

They are then worked with the fingers five times and then rinsed ten times under a tap at a flow rate of 4 l/minute with water at 38° C.

c. Results

A panel composed of 5 experts compared the feel on wet hair, of locks treated with formulation A3 relative to those treated with the comparative compositions (Reference 5/Reference 6).

Each expert evaluated the feel by classifying each of the locks treated with the comparative compositions (Reference 5/Reference 6) and the composition according to the invention (composition A3).

|  | Reference 5 | Reference 6 | A3 |
|---|---|---|---|
| Tester 1 | 2 | 3 | 1 |
| Tester 2 | 2 | 3 | 1 |
| Tester 3 | 2 | 3 | 1 |
| Tester 4 | 2 | 3 | 1 |
| Tester 5 | 2 | 3 | 1 |
| Overall classification | 2 | 3 | 1 |

The composition according to the invention (Composition A3) was systematically classified by the panel of testers as giving a smoother feel to the locks of treated hair than the comparative compositions (Reference 5/Reference 6).

IV. EXAMPLE—A4 VS REFERENCE 7/8

The following compositions are prepared from the ingredients indicated in the table below, the amounts of which are expressed as weight percentages relative to the total weight of the composition.

|  | Reference 7 | Reference 8 | A4 |
|---|---|---|---|
| Laureth-12 | 4 | 4 | 4 |
| Oxyethylenated lauric acid (4 OE) | 1 | 1 | 1 |
| Laureth-5 carboxylic acid | 6 | 6 | 6 |
| Coco betaine | 7 | 7 | 7 |
| Sodium ($C_{14}$-$C_{16}$)olefin sulfonate | 7 | 7 | 7 |

-continued

|  | Reference 7 | Reference 8 | A4 |
|---|---|---|---|
| Polydimethyldiallylammonium chloride Polyquaternium-6 | 0.5 | — | 0.5 |
| Polyquaternium-53 | — | 0.25 | 0.25 |
| Sodium chloride | 0.7 | 0.7 | 0.7 |
| Salicylic acid | 0.2 | 0.2 | 0.2 |
| Sodium benzoate | 0.5 | 0.5 | 0.5 |
| Sodium hydroxide/ Citric acid | qs pH 5 ± 0.5 | qs pH 5 ± 0.5 | qs pH 5 ± 0.5 |
| Water | qs 100 | qs 100 | qs 100 |

The compositions have a clear appearance, at the time of manufacture (t=t0), at room temperature.

The compositions are applied to locks of moderately sensitized hair (SA20) at a rate of 0.37 g of formulation/g of hair.

They are then worked with the fingers five times and then rinsed ten times under a tap at a flow rate of 4 l/minute with water at 38° C.

d. Results

A panel composed of 5 testers compared the feel on wet hair, of locks treated with formulation A4 relative to those treated with the comparative compositions (Reference 7/Reference 8).

Each tester evaluated the feel by classifying each of the locks treated with the comparative compositions (Reference 7/Reference 8) and the composition according to the invention (composition A4).

|  | Reference 7 | Reference 8 | A4 |
|---|---|---|---|
| Tester 1 | 2 | 3 | 1 |
| Tester 2 | 2 | 3 | 1 |
| Tester 3 | 2 | 3 | 1 |
| Tester 4 | 2 | 3 | 1 |
| Tester 5 | 2 | 3 | 1 |
| Overall classification | 2 | 3 | 1 |

The composition according to the invention (Composition A4) was systematically classified by the panel of testers as giving a smoother feel to the locks of treated hair than the comparative compositions (Reference 7/Reference 8).

V. EXAMPLE—A5

The following composition according to the invention is prepared from the ingredients indicated in the table below, the amounts of which are expressed as weight percentages relative to the total weight of the composition.

|  | A4 |
|---|---|
| Alkyl polyglucoside | 5.1 |
| Oxyethylenated lauric acid (4 OE) | 1 |
| Laureth-5 carboxylic acid | 6 |
| Cocamidopropylbetaine | 7 |
| Sodium laureth sulfate | 7 |
| Polydimethyldiallylammonium chloride Polyquaternium-6 | 0.75 |
| Polyquaternium-53 |  |
| Sodium chloride | 0.7 |
| Salicylic acid | 0.2 |
| Sodium benzoate | 0.5 |
| Sodium hydroxide/ Citric acid | qs pH 5 ± 0.5 |
| Water | qs 100 |

VI. EXAMPLE—A6 VS REFERENCE 9/10

The following compositions are prepared from the ingredients indicated in the table below, the amounts of which are expressed as weight percentages relative to the total weight of the composition.

|  | Reference 9 | Reference 10 | A6 |
|---|---|---|---|
| Lauryl ether carboxylic acid (4.5 OE) | 6 | 6 | 6 |
| Cocoylamidopropylbetaine | 7 | 7 | 7 |
| Oxyethylenated lauric acid (4 OE) | 1 | 1 | 1 |
| Oxyethylenated lauryl alcohol (12 OE) | 4 | 4 | 4 |
| Sodium lauryl ether sulfate | 7 | 7 | 7 |
| Polydimethyldiallylammonium chloride Polyquaternium-6 | 0.75 | — | 0.5 |
| Dimethyldiallylammonium chloride/acrylamide copolymer Polyquaternium-7 | — | 0.75 | 0.25 |
| Sodium chloride | 0.8 | 0.8 | 0.8 |
| Sodium benzoate | 0.5 | 0.5 | 0.5 |
| Salicylic acid | 0.2 | 0.2 | 0.2 |
| Citric acid | qs pH 4.7 | qs pH 4.7 | qs pH 4.7 |
| Water | qs 100 | qs 100 | qs 100 |

The compositions are applied to locks of moderately sensitized hair (SA20) at a rate of 0.37 g of composition per gram of hair. They are then worked with the fingers five times and then rinsed ten times under a tap at a flow rate of 4 l/minute with water at 38° C.

A panel of 5 experts compared the feel and the ease of the disentangling on wet hair, of locks treated with formulation A relative to those treated with the comparative compositions.

The invention claimed is:

1. A composition comprising:
   (i) at least one anionic surfactant chosen from carboxylic alkyl ether anionic surfactants corresponding to the polyethoxylated carboxylic anionic surfactants of formula (I):

$$R_1(OC_2H_4)_nOCH_2COOA \qquad (I)$$

wherein:
   $R_1$ is chosen from a linear or branched $C_8$-$C_{22}$ alkyl or alkenyl group or mixture of groups, a ($C_8$-$C_9$)alkylphenyl group, or a group $R_2CONH-CH_2-CH_2-$, wherein $R_2$ is a linear or branched $C_{11}$-$C_{21}$ alkyl or alkenyl group,
   n is an integer or decimal number that ranges from 2 to 24, and
   A is chosen from H, $NH_4$, $N_a$, K, Li, Mg, or a monoethanolamine or triethanolamine residue,
   (ii) at least one nonionic surfactant in a total amount of at least 3% by weight, relative to the total weight of the composition,
   (iii) at least one amphoteric surfactant in a total amount of at least 3% by weight, relative to the total weight of the composition,
   (iv) at least one cationic polymer with a cationic charge density of greater than or equal to 4 meq./g, and
   (v) at least one polymer chosen from amphoteric polymers and/or cationic polymers with a cationic charge density of less than 4 meq./g.

2. The composition according to claim 1, wherein the at least one anionic surfactant is a mixture of sulfate anionic surfactants chosen from $C_8$-$C_{14}$ alkyl ether sulfates, and carboxylic alkyl ether surfactants chosen from the polyethoxylated carboxylic anionic surfactants of formula (I):

$$R_1(OC_2H_4)_nOCH_2COOA \quad (I),$$

wherein:

$R_1$ is chosen from a linear or branched $C_8$-$C_{22}$ alkyl or alkenyl group or mixture of groups, a ($C_8$-$C_9$)alkylphenyl group, or a group $R_2CONH-CH_2-CH_2-$, wherein $R_2$ is a linear or branched $C_{11}$-$C_{21}$ alkyl or alkenyl group, n is an integer or decimal number that ranges from 2 to 24, and A is chosen from H, $NH_4$, Na, K, Li, Mg, or a monoethanolamine or triethanolamine residue.

3. The composition according to claim 1, wherein the at least one amphoteric surfactant is chosen from ($C_8$-$C_{20}$)alkylbetaines, ($C_8$-$C_{20}$)alkylsulfobetaines, ($C_8$-$C_{20}$)alkylamido($C_3$-$C_8$)alkylbetaines, or ($C_8$-$C_{20}$)alkylamido($C_6$-$C_8$) alkylsulfobetaines.

4. The composition according to claim 1, wherein the at least one nonionic surfactant is chosen from:

saturated or unsaturated, linear or branched, oxyethylenated $C_8$-$C_{40}$ alcohols comprising from 1 to 100 mol of ethylene oxide, and comprising one or two fatty chains;

saturated or unsaturated oxyethylenated vegetable oils comprising from 1 to 100 mol of ethylene oxide;

($C_8$-$C_{30}$)alkyl(poly)glucosides, which are optionally oxyalkylenated with 0 to 10 mol of ethylene oxide and comprising 1 to 15 glucose units;

monoglycerolated or polyglycerolated $C_8$ to $C_{40}$ alcohols, comprising from 1 to 50 mol of glycerol;

saturated or unsaturated, linear or branched, oxyalkylenated $C_8$-$C_{30}$ fatty acid amides;

esters of saturated or unsaturated, linear or branched, $C_8$-$C_{30}$ acids and of polyethylene glycols;

optionally oxyethylenated esters of saturated or unsaturated, linear or branched, $C_8$-$C_{30}$ acids and of sorbitol;

or mixtures thereof.

5. The composition according to claim 1, wherein the at least one cationic polymer with a charge density of greater than or equal to 4 meq./g and the at least one cationic polymer with a cationic charge density of less than 4 meq./g are chosen from:

(1) homopolymers or copolymers derived from acrylic or methacrylic esters or amides and comprising at least one of the units of formula (IX), (X), (XI) or (XII) below:

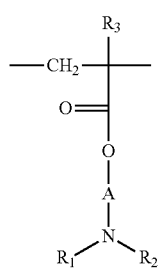
(IX)

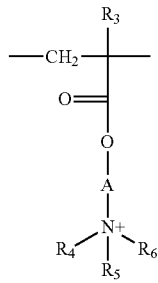
(X)

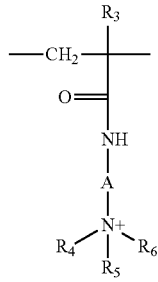
(XI)

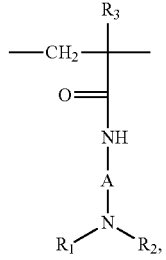
(XII)

wherein:

$R_3$, which may be identical or different, is chosen from a hydrogen atom or a $CH_3$ radical;

A, which may be identical or different, is chosen from a linear or branched alkyl group of 1 to 6 carbon atoms or a hydroxyalkyl group of 1 to 4 carbon atoms;

$R_4$, $R_5$ and $R_6$, which may be identical or different, are each chosen from an alkyl group containing from 1 to 18 carbon atoms, a benzyl radical, or an alkyl group containing from 1 to 6 carbon atoms;

$R_1$ and $R_2$, which may be identical or different, are each chosen from hydrogen, an alkyl group containing from 1 to 6 carbon atoms, methyl, or ethyl;

X is chosen from an anion derived from a mineral or organic acid, a methosulfate anion, a halide, chloride, or bromide;

(2) cyclopolymers of alkyldiallylamine or of dialkyldiallylammonium, chosen from homopolymers or copolymers comprising, as main constituent of the chain, units corresponding to formula (XIII) or (XIV):

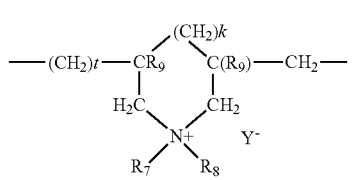
(XIII)

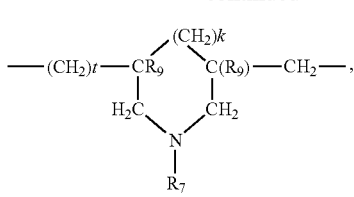

(XIV)

wherein:
k and t are equal to 0 or 1, the sum k+t being equal to 1;

$R_9$ is chosen from a hydrogen atom or a methyl radical;

$R_7$ and $R_8$, independently of each other, are each chosen from an alkyl group having from 1 to 6 carbon atoms, a hydroxyalkyl group in which the alkyl group contains 1 to 5 carbon atoms, a lower ($C_1$-$C_4$) amidoalkyl group;

or $R_7$ and $R_8$ may denote, together with the nitrogen atom to which they are attached, heterocyclic groups, piperidyl, or morpholinyl;

$Y^-$ is an anion chosen from bromide, chloride, acetate, borate, citrate, tartrate, bisulfate, bisulfite, sulfate, or phosphate;

(3) the quaternary diammonium polymer containing repeating units corresponding to formula (XV):

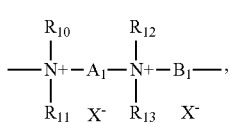

(XV)

wherein in formula (XV):

$R_{10}$, $R_{11}$, $R_{12}$ and $R_{13}$, which may be identical or different, are each chosen from aliphatic, alicyclic, or arylaliphatic radicals containing from 1 to 6 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

A1 and B1 represent polymethylene groups containing from 2 to 8 carbon atoms, which may be linear or branched and saturated or unsaturated and may contain, bonded to or intercalated in the main chain, at least one aromatic ring, or at least one oxygen or sulfur atom, or sulfoxide, sulfone, disulfide, amino, alkylamino, hydroxyl, quaternary ammonium, ureido, amide, or ester group, and $X^-$ is an anion derived from a mineral or organic acid;

A1, $R_{10}$ and $R_{12}$ can form, with the two nitrogen atoms to which they are attached, a piperazine ring; in addition, if A1 denotes a linear or branched, saturated or unsaturated alkylene or hydroxyalkylene radical, B1 can also denote a group —($CH_2$)n-CO-D-OC—($CH_2$)n- in which D denotes:

a) a glycol residue of formula: —O—Z—O—, where Z denotes a linear or branched hydrocarbon-based radical or a group corresponding to one of the following formulae:

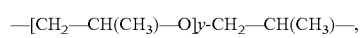

where x and y denote an integer from 1 to 4, representing a defined and unique degree of polymerization or any number from 1 to 4 representing an average degree of polymerization;

b) a bis-secondary diamine residue or a piperazine derivative;

c) a bis-primary diamine residue of formula: —NH—Y—NH—, where Y denotes a linear or branched hydrocarbon-based radical, or else the divalent radical —$CH_2$—$CH_2$—S—S—$CH_2$—$CH_2$—;

d) a ureylene group of formula: —NH—CO—NH—;

(4) polyquaternary ammonium polymers formed from repeating units of formula (XVII):

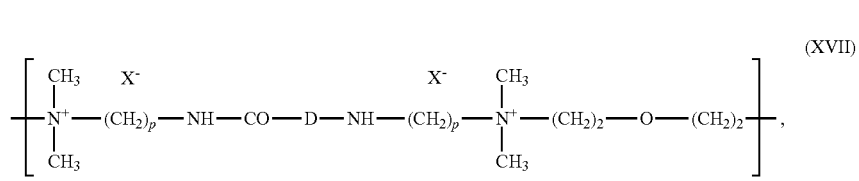

(XVII)

wherein:
p denotes an integer ranging from 1 to 6 approximately,
D may be nothing or may represent a group —($CH_2$)$_r$—CO— in which r denotes a number equal to 4 or 7, and
$X_-$ is an anion; or (5) quaternary polymers of vinylpyrrolidone and of vinylimidazole.

6. The composition according to claim 1, wherein the at least one cationic polymer with a charge density of greater than or equal to 4 meq./g is chosen from dialkyldiallylammonium halide homopolymers.

7. The composition according to claim 1, wherein the at least one amphoteric polymer comprises the repetition:
(i) of at least one unit from an acrylamide-type monomer,
(ii) of at least one unit from an acrylamidoalkyltrialkylammonium-type monomer,
(iii) of at least one unit derived from a monomer of (meth)acrylic acid type.

8. The composition according to claim 7, wherein the at least one unit derived from a monomer of acrylamide type in the at least one amphoteric polymer is chosen from units having the structure (XVIII) below:

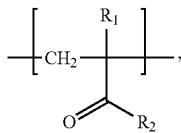 (XVIII)

wherein:
$R_1$ is chosen from H or $CH_3$,
$R_2$ is chosen from an amino, dimethylamino, tert-butylamino, or dodecylamino radical, or —NH—$CH_2OH$.

9. The composition according to claim 7, wherein the at least one unit derived from a monomer of acrylamidoalkyltrialkylammonium type in the at least one amphoteric polymer is chosen from units having the structure (XIX) below:

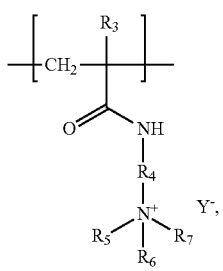 (XIX)

wherein:
$R_3$ is chosen from H or $CH_3$,
$R_4$ denotes a $(CH_2)_k$ group with k an integer ranging from 1 to 6;
$R_5$ and $R_6$ and $R_7$, which may be identical or different, each denote an alkyl group containing from 1 to 4 carbon atoms;
$Y^-$ is an anion chosen from bromide, chloride, acetate, borate, citrate, tartrate, bisulfate, bisulfite, sulfate, or phosphate.

10. The composition according to claim 7, wherein the at least one unit derived from a monomer of (meth)acrylic acid type in the at least one amphoteric polymer is chosen from units of formula (XX):

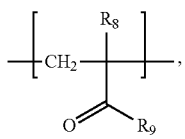 (XX)

wherein:
$R_8$ is chosen from H or $CH_3$,
$R_9$ is chosen from a hydroxyl radical or a radical —NH—$C(CH_3)_2$—$CH_2$—$SO_3H$.

11. The composition according to claim 1, wherein the at least one amphoteric polymer comprises:
from 30 mol % to 70 mol % of units derived from a monomer of acrylamide type,
from 10 mol % to 60 mol % of units derived from a monomer of acrylamidoalkyltrialkylammonium type, and
from 1 mol % to 20 mol % of units derived from a monomer of (meth)acrylic acid type.

12. The composition according to claim 1, wherein the at least one cationic polymer with a cationic charge density of less than 4 meq./g is chosen from copolymers of dimethyldiallylammonium halides and of acrylamide.

13. A process for washing and conditioning keratin fibres, the process comprising:
applying to said fibres a composition comprising:
(i) at least one anionic surfactant chosen from carboxylic alkyl ether anionic surfactants corresponding to the polyethoxylated carboxylic anionic surfactants of formula (I):

$$R_1(OC_2H_4)_nOCH_2COOA \quad (I)$$

wherein:
$R_1$ is chosen from a linear or branched $C_8$-$C_{22}$ alkyl or alkenyl group or mixture of groups, a $(C_8$-$C_9)$alkylphenyl group, or a group $R_2CONH$—$CH_2$—$CH_2$—, wherein $R_2$ is a linear or branched $C_{11}$-$C_{21}$ alkyl or alkenyl group,
n is an integer or decimal number that ranges from 2 to 24, and
A is chosen from H, $NH_4$, $N_a$, K, Li, Mg, or a monoethanolamine or triethanolamine residue,
(ii) at least one nonionic surfactant in a total amount of at least 3% by weight, relative to the total weight of the composition,
(iii) at least one amphoteric surfactant in a total amount of at least 3% by weight, relative to the total weight of the composition,
(iv) at least one cationic polymer with a cationic charge density of greater than or equal to 4 meq./g, and
(v) at least one polymer chosen from amphoteric polymers and/or cationic polymers with a cationic charge density of less than 4 meq./g.

14. A process for washing and conditioning hair, the process comprising:
applying to said hair a composition comprising:
(i) at least one anionic surfactant chosen from carboxylic alkyl ether anionic surfactants corresponding to the polyethoxylated carboxylic anionic surfactants of formula (I):

$$R_1(OC_2H_4)_nOCH_2COOA \quad (I)$$

wherein:
$R_1$ is chosen from a linear or branched $C_8$-$C_{22}$ alkyl or alkenyl group or mixture of groups, a $(C_8$-$C_9)$alkylphenyl group, or a group $R_2CONH$—$CH_2$—$CH_2$—, wherein $R_2$ is a linear or branched $C_{11}$-$C_{21}$ alkyl or alkenyl group,
n is an integer or decimal number that ranges from 2 to 24, and
A is chosen from H, $NH_4$, $N_a$, K, Li, Mg, or a monoethanolamine or triethanolamine residue,
(ii) at least one nonionic surfactant in a total amount of at least 3% by weight, relative to the total weight of the composition,
(iii) at least one amphoteric surfactant in a total amount of at least 3% by weight, relative to the total weight of the composition,
(iv) at least one cationic polymer with a cationic charge density of greater than or equal to 4 meq./g, and (v) at least one polymer chosen from amphoteric polymers and/or cationic polymers with a cationic charge density of less than 4 meq./g.

* * * * *